United States Patent
Han et al.

(10) Patent No.: US 10,822,543 B2
(45) Date of Patent: Nov. 3, 2020

(54) QUANTUM DOT HAVING CORE-SHELL STRUCTURE

(71) Applicant: KOREA ELECTRONICS TECHNOLOGY INSTITUTE, Seongnam-si, Gyeonggi-do (KR)

(72) Inventors: Chuljong Han, Yongin-si (KR); Byungwook Yoo, Seoul (KR); Jiyong Kim, Cheonan-si (KR); Jeongmin Yi, Suwon-si (KR)

(73) Assignee: KOREA ELECTRONICS TECHNOLOGY INSTITUTE, Seongnam-si (KR)

( * ) Notice: Subject to any disclaimer, the term of this patent is extended or adjusted under 35 U.S.C. 154(b) by 128 days.

(21) Appl. No.: 16/182,885

(22) Filed: Nov. 7, 2018

(65) Prior Publication Data
US 2019/0136130 A1     May 9, 2019

(30) Foreign Application Priority Data
Nov. 7, 2017 (KR) .......................... 10-2017-0147113

(51) Int. Cl.
| | |
|---|---|
| *H01B 1/06* | (2006.01) |
| *C09K 11/00* | (2006.01) |
| *C09K 11/70* | (2006.01) |
| *C09K 11/62* | (2006.01) |
| *H01L 31/0352* | (2006.01) |

(Continued)

(52) U.S. Cl.
CPC ................ *C09K 11/70* (2013.01); *B82Y 5/00* (2013.01); *B82Y 15/00* (2013.01); *C09K 11/025* (2013.01); *C09K 11/56* (2013.01); *C09K 11/623* (2013.01); *H01B 1/06* (2013.01); *H01L 31/035218* (2013.01)

(58) Field of Classification Search
CPC ........... H01B 1/00; H01B 1/06; H01L 33/502; H01L 51/502; C09K 11/0811; C09K 11/56; C09K 11/703; C09K 11/883
See application file for complete search history.

(56) References Cited

U.S. PATENT DOCUMENTS

| | | | |
|---|---|---|---|
| 2017/0247614 A1 | 8/2017 | Li et al. | |
| 2019/0115212 A1* | 4/2019 | Nadal | ................... C09K 11/883 |

FOREIGN PATENT DOCUMENTS

| | | | |
|---|---|---|---|
| CN | 103952137 A | * | 7/2014 |
| JP | 2017-122175 A | | 7/2017 |

(Continued)

OTHER PUBLICATIONS

Zhang et a; "Dual emissive Cu:InP/ZnS/InP/ZnS Nanocrystals . . . ", Chem. Mater. 2015, 27, 1405-1411.*

(Continued)

*Primary Examiner* — Mark Kopec
(74) *Attorney, Agent, or Firm* — Knobbe Martens Olson & Bear LLP (57) ABSTRACT

The present disclosure provides a quantum dot having a core-shell structure. To have superior quantum efficiency and optical stability, the quantum dot is of a five element system of Zn—Cu—In—P—S. The quantum dot includes a core formed of In(Zn)P material and doped with copper. The quantum dot further comprises a first shell formed of Cu—Zn—In—S material and surrounding the core and a second shell formed ZnS material and surrounding the first shell.

11 Claims, 12 Drawing Sheets

(51) Int. Cl.
*B82Y 5/00* (2011.01)
*B82Y 15/00* (2011.01)
*C09K 11/56* (2006.01)
*C09K 11/02* (2006.01)

(56) References Cited

FOREIGN PATENT DOCUMENTS

| KR | 10-2010-0071700 A | 6/2010 |
| KR | 10-2017-0041734 A | 4/2017 |
| KR | 10-2017-0080795 A | 7/2017 |
| WO | 2016/023820 A1 | 2/2016 |
| WO | 2017/019789 A1 | 2/2017 |

OTHER PUBLICATIONS

Hie et al "Synthesis of Cu-doped InP nanocrystals (d-dots) with ZnSe diffusion barrier as efficient and color-tunable NIR emitters", J.Am. Chem. Soc. 2009, 131, 10645-10651.*
Extended European Search Report of corresponding Patent Application No. 18204992.4—10 pages (dated Mar. 19, 2019).
Xie et al., "Synthesis of Cu-Doped InP Nanocrystals (d-dots) with ZnSe Diffusion Banier as Efficient and Color-Tunable NIR Emitters", J. Am. Chem. Soc., vol. 131, No. 30—7 pages (2009).
Park et al., "CuInS2/ZnS core/shell quantum dots by cation exchange and their blue-shifted photoluminescence", Journals of Materials Chemistry, vol. 21, No. 11—6 pages (2011).
Park et al., "Highly Bright Yellow-Green-Emitting CuInS2 Colloidal Quantum Dots with Core/Shell/Shell Architecture for White Light-Emitting Diodes", ACS Applied Materials & Interfaces, vol. 7, No. 12—8 pages (2015).
Notice of Allowance of corresponding Korean Patent Application No. 10-2017-0147113—5 pages (dated Jun. 18, 2019), (No English language translation).
Pradhan et al., "An Alternative of CdSe Nanocrystal Emitters: Pure and Tunable Impurity Emissions in ZnSe Nanocrystals", Journal of the American Chemical Society, vol. 127, No. 50—2 pages (2005), (Abstract Only).
Xie et al., "Synthesis of Cu-Doped InP Nanocrystals (d-dots) with ZnSe Diffusion Barrier as Efficient and Color-Tunable NIR Emitters", Journal of the American Chemical Society, vol. 131, No. 30—2 pages (2009), (Abstract Only).
Park et al., "CuInS2/ZnS core/shell quantum dots by cation exchange and their blue-shifted photoluminescence", Journal of Materials Chemistry, vol. 21, No. 11—4 pages (2011), (Abstract Only).
Park et al., "Highly Bright Yellow-Green-Emitting CuInS2 Colloidal Quantum Dots with Core/Shell/Shell Architecture for White Light-Emitting Diodes", ACS Applied Materials & Interfaces, vol. 7, No. 12—2 pages (2015), (Abstract Only).

* cited by examiner

| Indium ratio | Corrected quantum Efficiency (Internal) | Peak wavelength [nm] | FWHM [nm] |
|---|---|---|---|
| 0 | 32.0% | 685 | 132 |
| 0.5 | 45.7 % | 682 | 139 |
| 1 | 45.8 % | 680 | 135 |
| 1.5 | 53.8 % | 685 | 141 |
| 2.0 | 54.4 % | 682 | 138 |
| 2.5 | 57.2 % | 682 | 140 |

◆ Cu 1 eq fixed
◆ Zn 8 eq fixed

| | PL | FWHM | QY |
|---|---|---|---|
| In(Zn)P | 521nm | 57.5nm | 24.7% |
| Cu:In(Zn)P | 688nm | 119.25nm | 8.9% |

| | PL | FWHM | QY |
|---|---|---|---|
| Cu:In(Zn)P | 688nm | 119.25nm | 8.9% |
| Cu:In(Zn)P@ZCIS | 709.4nm | 140.97nm | 33.25% |

|  | PL | FWHM | QY |
|---|---|---|---|
| Cu:In(Zn)P@ZCIS | 709.4nm | 140.97nm | 33.25% |
| Cu:In(Zn)P@ZCIS@ZnS | 705.4nm | 146.57nm | 57% |

| Name | J values | Peak BE | Reference |
|---|---|---|---|
| In3d3 | 3d5/2 | 444.5 | Science 260, 1653 (1993) |

QUANTUM DOT HAVING CORE-SHELL STRUCTURE

CROSS-REFERENCE TO RELATED APPLICATION

The present application claims the benefit of priority to Korean Patent Application No. 10-2017-0147113, filed on Nov. 7, 2017, in the Korean Intellectual Property Office, the disclosure of which is incorporated herein in its entirety by reference.

TECHNICAL FIELD

The present disclosure relates to a quantum dot and, more particularly, to a quantum dot having a core-shell structure exhibiting superior quantum efficiency and optical stability.

BACKGROUND

A quantum dot is a semiconductor crystalline material having a size of several nanometers and being composed of hundreds to thousands of atoms. Such a small-sized material, in which a surface area per unit volume is large and most of the atoms are present on or near its surface, exhibits a quantum confinement effect and has electronic, magnetic, optical, chemical, and mechanical properties different from those of a bulk semiconductor material.

Impurities contained in the quantum dot may strongly change the electronic, optical, and magnetic properties of the semiconductor. In particular, a doped semiconductor used in a solar cell or a luminescent solar concentrator (LSC) which requires a long-lasting light source transports electrons excitated by absorbed energy more faster and efficiently to the impurities and quickly forms excitons so as to suppress photo-oxidative degradation or photodecomposition resulting from an interference at surface energy levels and improve the stability. See Narayan Pradhan et al., *J. Am. Chem. Soc.*, 127: 17586-17587, 2005.

Cadmium-based quantum dot materials such as cadmium telluride (CdTe) may exhibit a tunable spectrum, be implemented in a visible light range, and have high quantum efficiency, but are disadvantageous in that cadmium ions can accumulate over time in human bodies and thus are environmentally dangerous.

Accordingly, in order to solve this problem, cadmium-free quantum dots are being studied actively. For example, quantum dots made from indium phosphide (InP) or copper indium zinc sulfide (Cu—In—Zn—S) have been under active studies and are known as more environment-friendly quantum dot materials compared with commercially available cadmium-based quantum dots.

A quantum dot having indium phosphide (InP) core doped with copper and having a zinc selenide (ZnSe) or zinc sulfide (ZnS) shell are reported to have a quantum yield around 30-40%. See Renguo Xie et al., *J. Am. Chem. Soc.*, 131: 10645-10651, 2009. Meanwhile, it is known that the copper exhibits higher stability against the photodecomposition than the indium phosphilde (InP), but the Cu:InP/ZnSe or Cu:InP/ZnS quantum dots are reported that a copper content relative to an InP content exhibiting is as low as 20% at maximum, and thus are relatively unfavorable in terms of the stability against the photodecomposition.

Quantum dots having copper indium zinc sulfide (Cu—In—Zn—S) or copper indium sulfide (Cu—In—S) cores have a limited emission range from the visible light range to an infrared range near 700 nm. Also, the copper content is limited in these quantum dots since the content of copper influences on a band gap of the cores which determines the emission range of the cores. Further, since the formation of the zinc sulfide (ZnS) shell induces a spectrum-shift towards blue, it may be difficult to form an infrared range in the emission spectrum. See Jaehyun Park et al., *J. Mater. Chem.*, 21: 3745-3750, 2011; Sang Hyun Park et al., *ACS. Appl. Mater. Interfaces*, 7: 6764-6771, 2015.

SUMMARY

According to the present disclosure, provided is a quantum dot that has a core-shell structure and exhibits superior quantum efficiency and optical stability.

Additional aspects will be set forth in part in the description which follows and, in part, will be apparent from the description, or may be learned by practice of the presented exemplary embodiments.

According to an aspect of an exemplary embodiment, a quantum dot having a core-shell structure, includes: a core formed of In(Zn)P (or InZnP) material and doped with copper; and a shell formed of Cu—Zn—In—S material and surrounding the core.

The copper content in the quantum dot may be 20 wt % or more.

A band gap of the core may be included in a band gap of the shell.

A spectrum shift towards red may occur in an emission wavelength range as a size of the core increases.

An emission wavelength range of the core may be shifted towards red due to the shell.

A quantum efficiency of the quantum dot may increase as an increase in a content of indium in the shell. The change in a peak of the emission wavelength range may be within ±5 nm.

According to an aspect of another exemplary embodiment, a quantum dot having a core-shell structure, includes: a core formed of In(Zn)P material and doped with copper; a first shell formed of Cu—Zn—In—S material and surrounding the core; and a second shell formed ZnS material and surrounding the first shell.

According to an aspect of yet another exemplary embodiment, a quantum dot having a core-shell structure is composed of a five element system of Zn—Cu—In—P—S.

According to the present disclosure, the quantum efficiency can be improved by forming the shell of Cu—Zn—In—S element system on the core formed of In(Zn)P material doped with copper.

The copper content in the quantum dot according to the present disclosure may be increased due to its structure in which a shell composed of Cu—Zn—In—S element system is formed on the core. As a result, the optical stability of the quantum dot can be enhanced.

The light emission wavelength range of the quantum dot according to the present disclosure depends on a band gap of the core doped with copper and can be controlled to extend to an infrared region corresponding to a band gap around 1.21 eV.

The quantum efficiency of the quantum dot according to the present disclosure may is improved further because of the second shell surrounding the first shell and formed of ZnS, which has little lattice mismatches, is non-toxic, and has a higher chemical stability and a wider band gap than the Cu—Zn—In—S element system.

BRIEF DESCRIPTION OF THE DRAWINGS

In order that the disclosure may be well understood, there will now be described various forms thereof, given by way of example, reference being made to the accompanying drawings, in which.

The drawings described herein are for illustration purposes only and are not intended to limit the scope of the present disclosure in any way.

DETAILED DESCRIPTION

In the following description and the accompanied drawings, detailed descriptions of well-known functions or configuration that may obscure the subject matter of the present disclosure will be omitted for simplicity. It is to be noted that the same components are designated by the same reference numerals throughout the drawings.

The terms and words used in the following description and appended claims are not necessarily to be construed in an ordinary sense or a dictionary meaning, and may be appropriately defined herein to be used as terms for describing the present disclosure in the best way possible. Such terms and words should be construed as meaning and concept consistent with the technical idea of the present disclosure. The embodiments described in this specification and the configurations shown in the drawings are merely preferred embodiments of the present disclosure and are not intended to limit the technical idea of the present disclosure. Therefore, it should be understood that there may exist various equivalents and modifications which may substitute the exemplary embodiments at the time of filing of the present application.

Herein below, exemplary embodiments of the present disclosure will be described in detail with reference to the accompanying drawings.

FIG. 1A, FIG. 1B, FIG. 1C and FIG. 1D illustrate steps of manufacturing a quantum dot having a core-shell structure according to the present disclosure.

Referring to FIGS. 1A-1D, the quantum dot 100 according to the present disclosure has a core-shell structure and is a five-element system composed of zinc(Zn)-copper (Cu)-Indium (In)-phosphorus (P)-sulfur (S). The quantum dot 100 includes a core 30 made of In(Zn)P doped with copper 20 and a first shell 40 made of Cu—Zn—In—S and surrounding the core 30. In embodiments, the quantum dot 100 further includes a second shell 50 made of zinc sulfide (ZnS) surrounding the first shell 40.

The quantum dot 100 according to the present disclosure has a copper content of 20 wt % or more. As a result, the quantum dot 100 according to the present disclosure has good optical stability.

The quantum dot 100 according to the present disclosure is composed of Cu—In—Zn—P—S which is more environment-friendly than the cadmium-based quantum dot and has an emission wavelength range in the visible light range to the infrared range. Thus, the quantum dot 100 can be applied to biomedical imaging applications, for example. The quantum dot 100 according to the present disclosure can also be applied to doping to induce magnetic properties. The energy levels of the dopants confined in the quantum dot material enhances the binding energy of the carrier and increases quantummechanical spins.

Since the quantum dot 100 according to the present disclosure has the core 30 made of the In(Zn)P doped with copper 20 and the Cu—Zn—In—S first shell 40 formed on the core 30, the quantum dot 100 may have an improved quantum efficiency.

Since the first shell 40 composed of the Cu—Zn—In—S element system is formed on the core 30, the concentration of copper 20 in the core 30 can be increased in the quantum dot 100 according to the present disclosure. As a result, the optical stability of the quantum dot 100 can be enhanced.

The light emission wavelength range of the quantum dot 100 according to the present disclosure depends on a band gap of the core 30 formed of In(Zn)P and doped with copper 20 and can be controlled to extend to an infrared region corresponding to a band gap around 1.21 eV.

The quantum efficiency of the quantum dot 100 according to the present disclosure is improved further because of the second shell 50 surrounding the first shell 40 and formed of ZnS, which has little lattice mismatches, is non-toxic, and has a higher chemical stability and a wider band gap than the Cu—Zn—In—S element system.

The quantum dot 100 according to the present disclosure may be manufactured as follows.

Figure 1A:
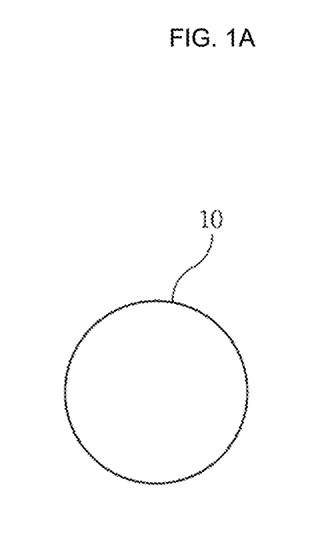
FIG. 1A, FIG. 1B, FIG. 1C and FIG. 1D illustrate steps of manufacturing a quantum dot having a core-shell structure according to the present disclosure.

First, the core material 10 is prepared as shown in FIG. 1A. In(Zn)P material which is more environment-friendly than cadmium-based core material is used for the core material 10.

Figure 1B:
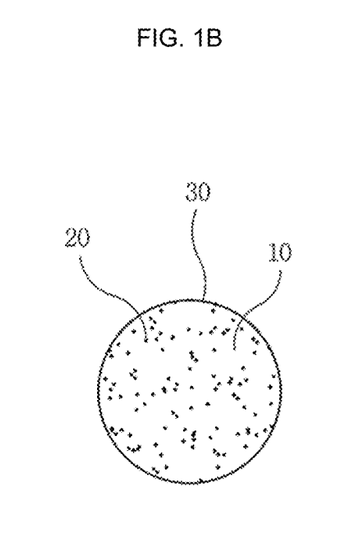

Next, as shown in FIG. 1B, the core 30 is synthesized by doping the core material 20 with copper 20 that enables an emission in a near-infrared region above a wavelength of 600 nm and has a high stability against photodegradation. Here, the core 30 doped with copper based on the In(Zn)P material is denoted by Cu:In(Zn)P.

Figure 1C:
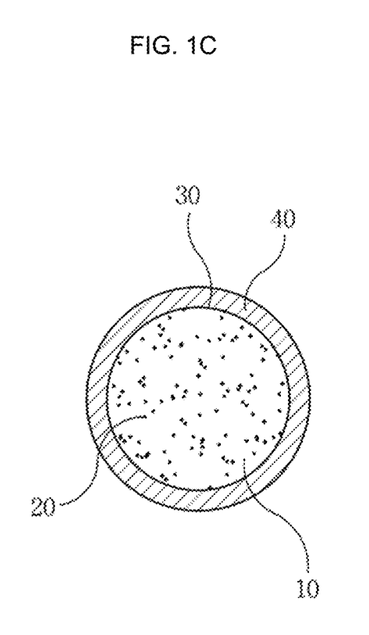

Subsequently, as shown in FIG. 1C, a first shell 40 of Cu—Zn—In—S material is formed to surround the core 30.

A conventional method of overcoating a ZnSe shell has disadvantages of low quantum efficiency of less than 40% and low optical stability. To solve the problems, in the present disclosure, the first shell 40 is formed by overcoating Cu—Zn—In—S material having a relatively high copper content on the surface of the core 30. The use of Cu—Zn—In—S material for the first shell 40 formed on the core portion 30 improves the quantum efficiency and the optical stability compared with the case of using ZnSe for the first shell 40. The combination of the core 30 and the first shell 40 may be denoted by Cu:In(Zn)P/Zn—Cu—In—S or Cu:In(Zn)P@Zn—Cu—In—S.

Figure 1D:
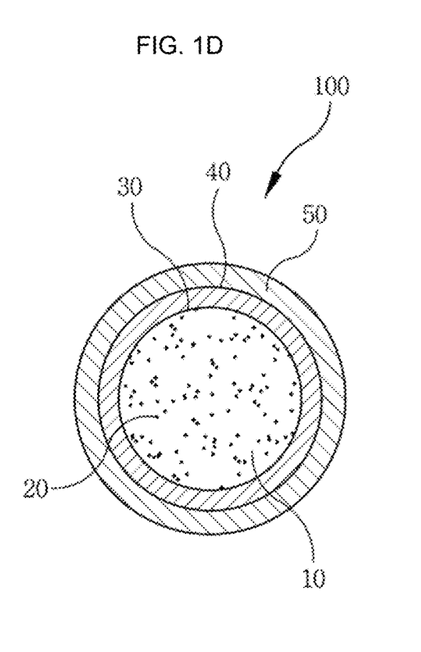

The manufacturing of the quantum dot 100 according to the present disclosure may be completed by forming the second shell 50 of ZnS material to surround the first shell 40 as illustrated in FIG. 1D. The second shell 50 made of ZnS has little lattice mismatches with the first shell 40 made of Cu—Zn—In—S, is non-toxic, and enhances the quantum efficiency of the quantum dot 100 since it has a wider band gap than the Cu—Zn—In—S element system.

The structure of the quantum dot 100 according to the present disclosure including the core 30, the first shell 40, and the second shell 50 may be denoted by Cu:In(Zn)P/Zn—Cu—In—S/ZnS or Cu:In(Zn)P@Zn—Cu—In—S@ZnS.

The quantum efficiency and the optical stability of the quantum dot 100 according to the present disclosure will now be described with reference to FIG. 1A-FIG. 3.

Figure 2:
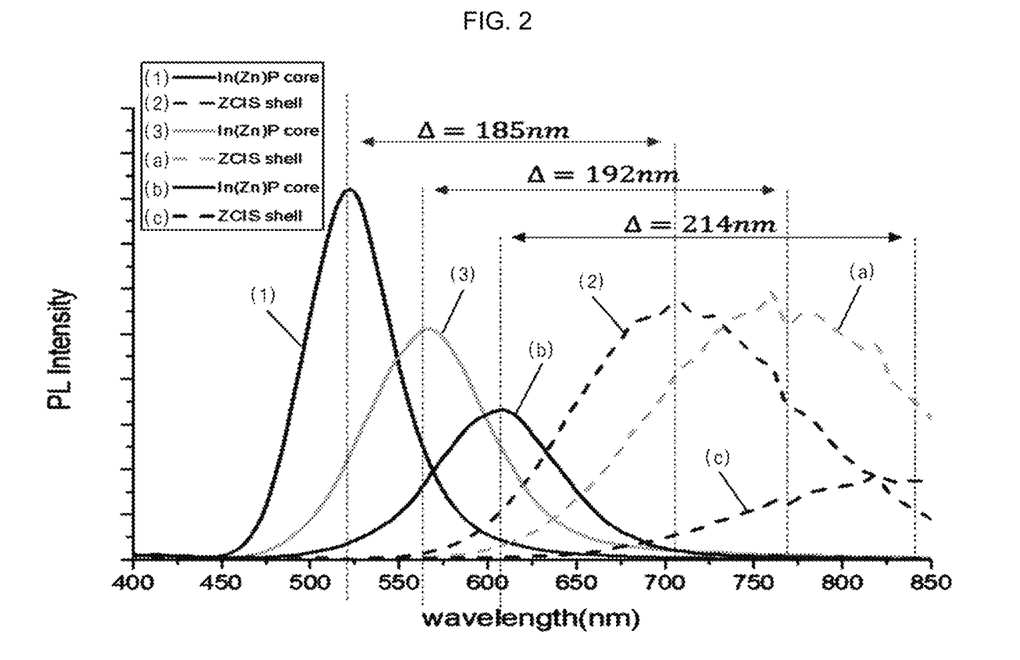
FIG. 2 is a graph showing changes in emission ranges depending on core and first shell materials in a quantum dot according to the present disclosure.

Referring to FIGS. 1A-2, the emission wavelength range of the first shell 40 is determined depending on the band gap of the core 30. Here, FIG. 2 is a graph showing changes in emission wavelength ranges depending on the core 30 and the first shell 40 in the quantum dot 100 according to the present disclosure. In FIG. 2, reference symbols (1), (2), and (3) indicate three cases of the core 100 having different sizes, and the sizes of the core 100 increase in an order of (1)<(2)<(3). The first shells 40 formed on the cores 100 denoted by (1), (2), and (3) are denoted by (a), (b), (c), respectively.

It can be seen in the drawing that a spectrum shift towards red due to the doping of the copper 20 occurs in the emission wavelength range as the size of the core 30 increases. As a result, the red shift in the emission wavelength range can be found in the first shell 40 also.

Figure 3A:
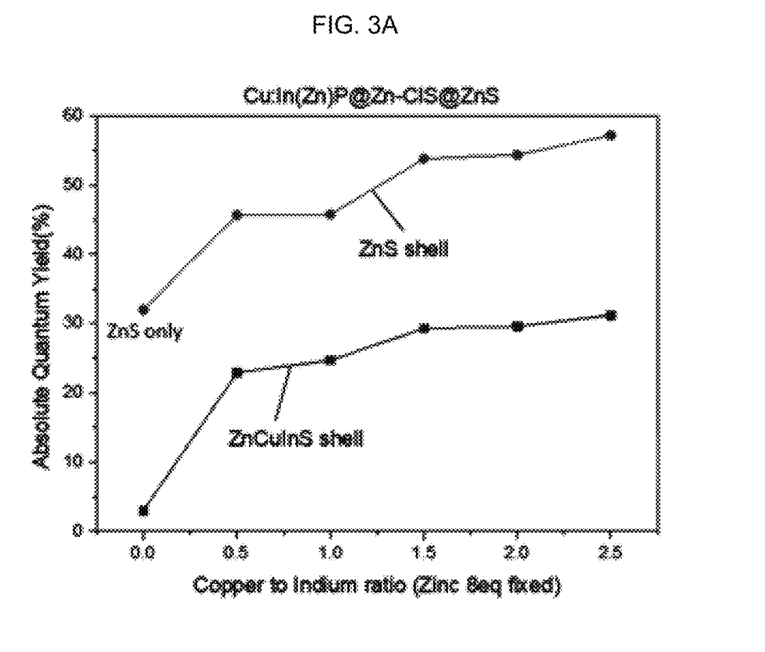
FIG. 3A and FIG. 3B show a change in a quantum efficiency according to an increase in an indium content in a first shell of a quantum dot according to a first example of the present disclosure.
Figure 3B:
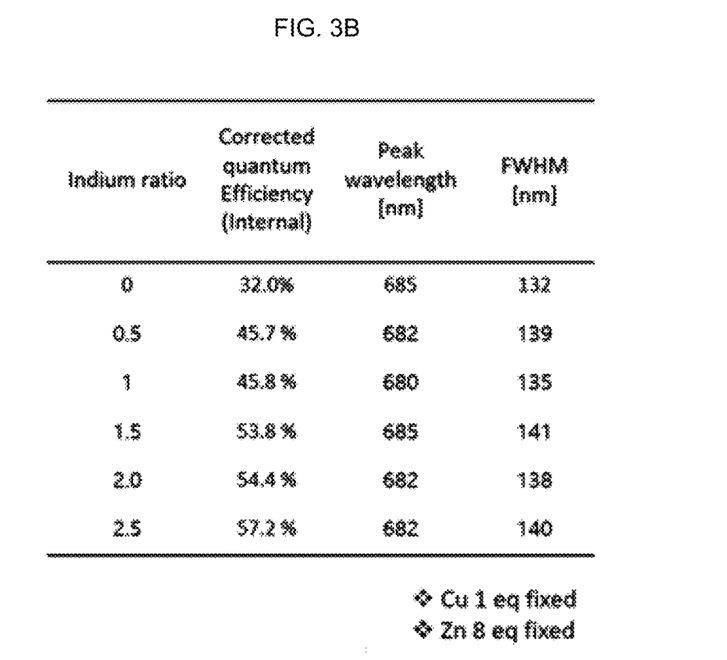

Meanwhile, as shown in FIGS. 1A-1D, FIG. 2, FIG. 3A and FIG. 3B, the quantum efficiency of the first shell 40 increases with the increase in an indium content in the first shell 40. FIG. 3A and FIG. 3B shows a change in the quantum efficiency according to an increase in the indium content in the first shell 40 of the quantum dot 100 according to the present disclosure.

In other words, it can be seen from the drawing that the increase in the indium content while the first shell 40 is formed enhances the quantum efficiency. Also, it can be found that the change in the peak of the emission wavelength range of the first shell 40 is within ±5 nm. That is, the quantum dot material formed with the first shell 40 exhibits little change in the peak of the emission wavelength range. This means that indium introduced in the process of forming the first shell 40 does not substantially affect the core 30.

Therefore, it is indirectly confirmed that the Zn—Cu—In—S material does not replace the function of the core 30 but just forms the first shell 40 on the surface of the core 30.

In order to evaluate the quantum efficiency and the optical stability of the quantum dot according to the present disclosure, quantum dots according to the following examples were prepared.

Before the description of examples, it should be noted that the first shell made of Zn—Cu—In—S elements system does not determine the emission wavelength range, but the emission wavelength range of the quantum dot having the structure of Cu:In(Zn))P/Zn—Cu—In—S/ZnS is determined by the emission wavelength range of the Cu:In(Zn)P core.

Thus, it is now described in detail that three emission wavelength ranges can be implemented through Examples 1-3, and the quantum efficiency and the optical stability thereof will be described later.

The steps of preparing the quantum dots according to Examples 1 through 3 may be summarized briefly as follows.

Example 1

A Cu:In(Zn))P/Zn—Cu—In—S/ZnS quantum dot having an emission wavelength range of 700 nm is manufactured as follows.
Step 1-1: 521 nm InP
Step 1-2: 688 nm Cu:In(Zn)P
Step 1-3: 709.4 nm Cu:In(Zn))P/Zn—Cu—In—S
Step 1-4: 705.4 nm Cu:In(Zn))P/Zn—Cu—In—S/ZnS

Example 2

A Cu:In(Zn))P/Zn—Cu—In—S/ZnS quantum dot having an emission wavelength range of 760 nm is manufactured as follows.
Step 2-1: 568 nm InP
Step 2-2: 741 nm Cu:In(Zn)P
Step 2-3: 760 nm Cu:In(Zn))P/Zn—Cu—In—S
Step 2-4: 760 nm Cu:In(Zn))P/Zn—Cu—In—S/ZnS

Example 3

A Cu:In(Zn))P/Zn—Cu—In—S/ZnS quantum dot having an emission wavelength range of 840 nm is manufactured as follows.
Step 3-1: 620 nm InP
Step 3-2: 822 nm Cu:In(Zn)P
Step 3-3: 840 nm Cu:In(Zn))P/Zn—Cu—In—S
Step 3-4: 840 nm Cu:In(Zn))P/Zn—Cu—In—S/ZnS The steps of manufacturing the quantum dots according to Examples 1 through 3 will now be described in detail.

Example 1

First, the core material of 521 nm In(Zn)P according to the step 1-1 is prepared as follows.

1 millimoles (mmol) of indium acetate, 1 mmol of zinc acetate, and 2 ml of oleic acid are put in a reactor and heated at 130° C. under vacuum for 2 hours. After heating, the temperature of the reactor is lowered to 50° C., 15 ml of 1-octadecene is injected thereto, and the mixture is heated at 120° C. for 1 hour. Then, an atmosphere in the reactor is converted into nitrogen and then cooled to room temperature.

Next, a mixed solution of tris(trimethylsilyl)phosphine (TMS3P, 1 mmol) and 1-octadecene (9 ml) is prepared and injected into the reactor. Subsequently, the reactor is subjected to a heat treatment while being gradually heated up to 300° C. at a rate of 20° C./min to synthesize a 521 nm In(Zn)P core material according to the step 1-1.

The core material of 688 nm Cu:In(Zn)P according to the step 1-2 is prepared as follows.

5 mmol of copper acetate, 3 ml of oleic acid, and 10 ml of 1-octadecene are mixed and put in a 100 ml round-bottomed flask and heated at 130° C. under vacuum for 2 hours. Then, the reactor is cooled to room temperature to prepare a 0.5 M copper oleate stock solution.

Then, 2 ml (1 mmol) of a 0.5 M copper oleate stock solution previously prepared in a one pot reaction is injected into a flask containing the core material of 521 nm In(Zn)P synthesized in the step 1-1. The reaction is carried out at 200° C. for 1 hour to prepare the core of 688 nm Cu:In(Zn)P according to the step 1-2.

The quantum dot material of 709.4 nm Cu:In(Zn))P/Zn—Cu—In—S according to the step 1-3 is prepared as follows.

First, 5 mmol of indium acetate, 5 ml of oleic acid, and 10 ml of 1-octadecene are put in a 100 ml round-bottomed flask and heated at 130° C. under vacuum for 2 hours. Then, the solution is cooled to room temperature to prepare a 0.5 M indium oleate stock solution.

Next, 5 mmol of zinc acetate, 3.5 ml of oleic acid, and 10 ml of 1-octadecene are put in a 100 ml round-bottomed flask and heated at 130° C. under vacuum for 2 hours. Then, the solution is cooled to room temperature to prepare a stock solution of 0.5 M zinc oleate.

Subsequently, 4 ml (2 mmol) of 0.5 M indium oleate solution, 2 ml (1 mmol) of 0.5 M copper oleate solution, 0.5 M 4 ml (2 mmol) of oleandan zinc, and 0.5 ml of 1-dodecanethiol are added to the flask in which the synthesized in the step 1-2 is put. The mixture is gradually heated up to 230° C. at a rate of 10° C./min and allowed to react at 230° C. for 1 hour.

Then, the temperature is lowered to room temperature to prepare a quantum dot material of Cu:In(Zn))P/Zn—Cu—In—S having the first shell of Zn—Cu—In—S according to the step 1-3.

The quantum dot material of 705.4 nm Cu:In(Zn))P/Zn—Cu—In—S/ZnS according to the step 1-4 is prepared as follows.

8 ml of 0.5 M zinc oleate previously prepared in a one pot reaction is added to a flask containing the quantum dot material of Cu:In(Zn)P/Zn—Cu—In—S synthesized in the step 1-3, and the temperature is raised to 230° C. 4 ml of 1-dodecanethiol is rapidly injected to the hot solution, and the mixture is allowed to react while being stirred for 2 hours.

Then, the temperature is lowered to room temperature to complete the manufacturing of the Cu:In(Zn))P/Zn—Cu—In—S/ZnS quantum dot according to the Example 1 having the second shell of ZnS according to the step 1-4.

Example 2

First, the core material of 568 nm In(Zn)P according to the step 2-1 is prepared as follows.

1.6 mmol of indium acetate, 1 mmol of zinc acetate, and 2 ml of oleic acid are put in a reactor and heated at 130° C. under vacuum for 2 hours. After heating, the temperature of the reactor is lowered to 50° C., 15 ml of 1-octadecene is injected thereto, and the mixture is heated at 120° C. for 1 hour. Then, an atmosphere in the reactor is converted into nitrogen and then cooled to room temperature.

Next, a mixed solution of tris(trimethylsilyl)phosphine (0.8 mmol) and 1-octadecene (9 ml) is prepared and injected into the reactor. Subsequently, the reactor is subjected to a heat treatment while being gradually heated up to 300° C. at a rate of 20° C./min to synthesize a 568 nm In(Zn)P core material according to the step 2-1.

After the step 2-1, the steps 2-2 to 2-4 are carried out in the same manner as the steps 1-2 to 1-4, respectively, so as to prepare the 741 nm Cu:In(Zn)P core material according to the step 2-2 and the 760 nm Cu:In(Zn)P/Zn—Cu—In—S quantum dot material having the first shell of Zn—Cu—In—S according to the step 2-3, and finally manufacture the 760 nm Cu:In(Zn)P/Zn—Cu—In—S/ZnS quantum dot according to the Example 2 of the present disclosure having second shell of ZnS according to step 2-4.

Example 3

First, the core material of 620 nm In(Zn)P according to the step 3-1 is prepared as follows.

2.5 mmol of indium acetate, 1 mmol of zinc acetate, and 2 ml of oleic acid are put in a reactor and heated at 130° C. under vacuum for 2 hours. After heating, the temperature of the reactor is lowered to 50° C., 15 ml of 1-octadecene is injected thereto, and the mixture is heated at 120° C. for 1 hour. Then, an atmosphere in the reactor is converted into nitrogen and then cooled to room temperature.

Next, a mixed solution of tris(trimethylsilyl)phosphine (1 mmol) and 1-octadecene (9 ml) is prepared and injected into the reactor. Subsequently, the reactor is subjected to a heat treatment while being gradually heated up to 300° C. at a rate of 20° C./min to synthesize a 620 nm In(Zn)P core material according to the step 3-1.

After the step 3-1, the steps 3-2 to 3-4 are carried out in the same manner as the steps 1-2 to 1-4, respectively, so as to prepare the 822 nm Cu:In(Zn)P core material according to the step 3-2 and the 840 nm Cu:In(Zn)P/Zn—Cu—In—S quantum dot material having the first shell of Zn—Cu—In—S according to the step 3-3, and finally manufacture the 840 nm Cu:In(Zn)P/Zn—Cu—In—S/ZnS quantum dot according to the Example 3 having second shell of ZnS according to step 3-4.

The steps of manufacturing the quantum dot according to the first example of the present disclosure will now be described in detail with reference to FIGS. 4-13.

Figure 4A:
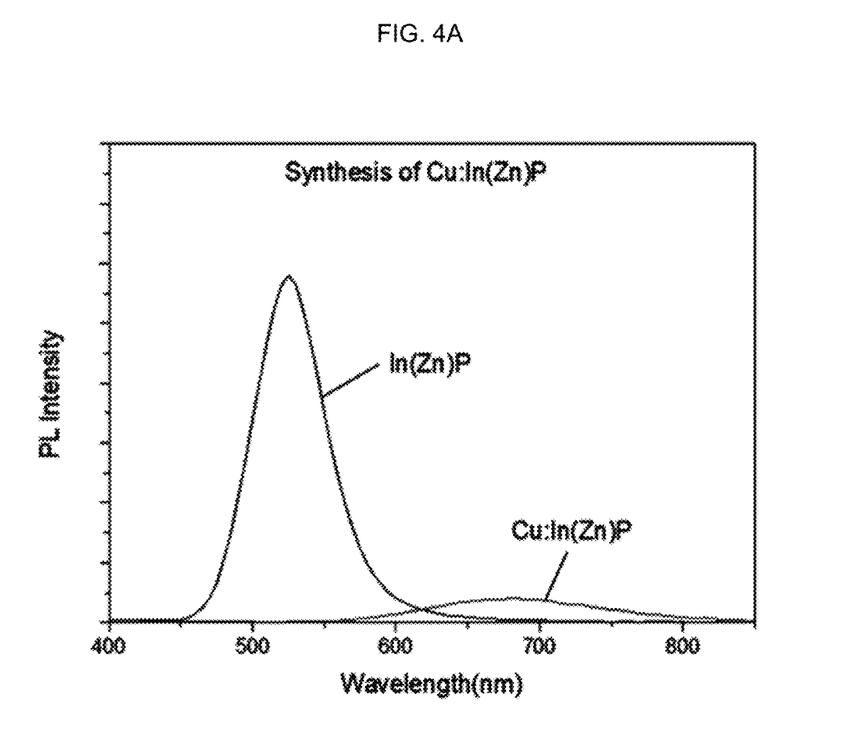
FIG. 4A and FIG. 4B illustrate changes in characteristics of the core according to copper doping in a quantum dot prepared in the Example 1 of the present disclosure.
Figure 4B:
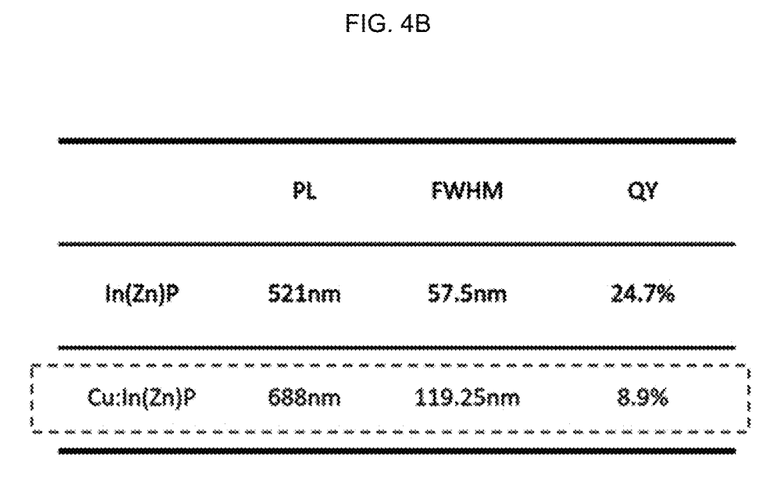

FIG. 4A and FIG. 4B illustrate changes in characteristics of the core according to copper doping in a quantum dot prepared in the Example 1 of the present disclosure.

Referring to FIG. 4A and FIG. 4B, the Cu:In(Zn)P core is synthesized according to the step 1-2 by doping copper in the core material of In(Zn)P prepared in the step 1-1. As energy levels of copper are inserted into the band gap of In(Zn)P core material during a copper doping process, the Cu:In(Zn)P core has an increased full width at half maximum (FWHM) and a red-shifted emission wavelength range.

Figure 5A:
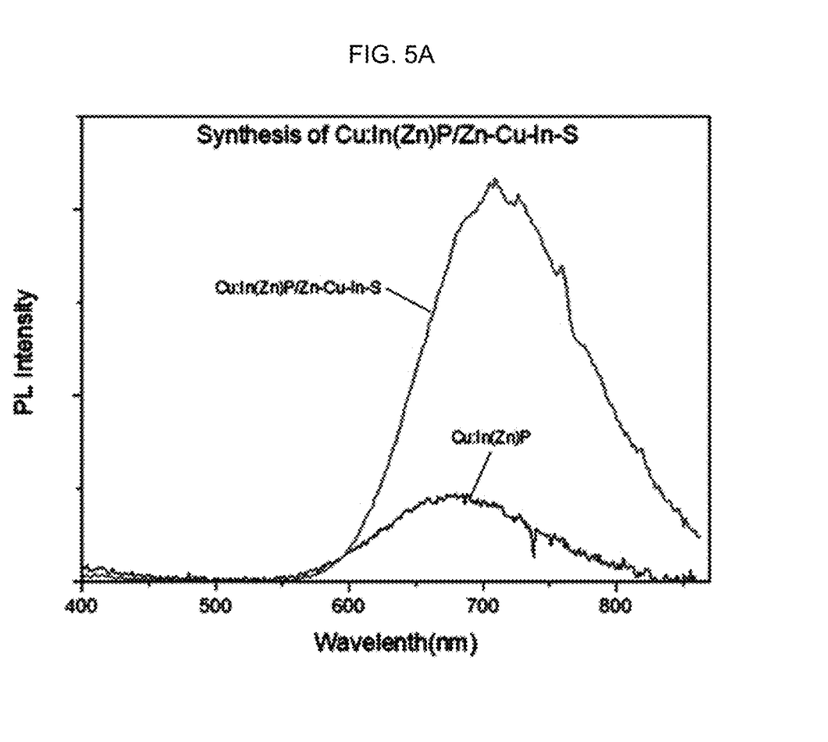
FIG. 5A and FIG. 5B illustrate changes in changes in properties of a quantum dot according to the synthesis of a first shell in the quantum dot prepared in the Example 1 of the present disclosure.
Figure 5B:
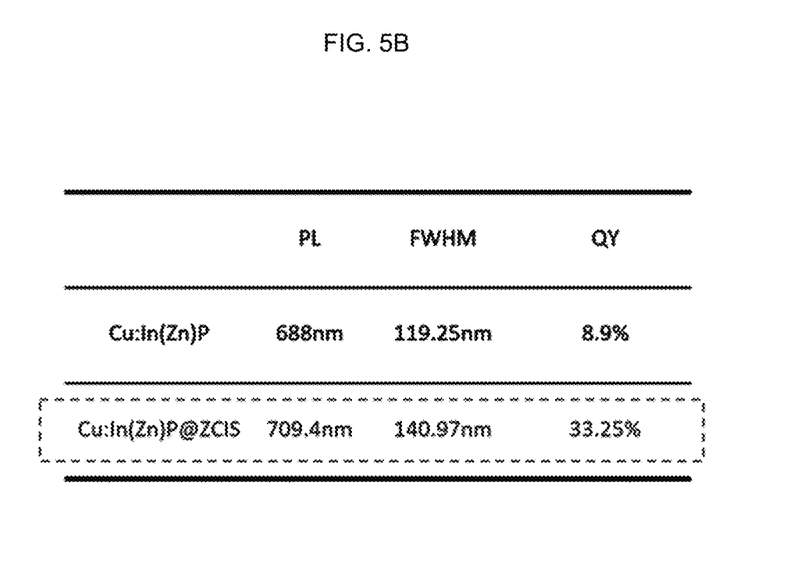

FIG. 5A and FIG. 5B illustrate changes in changes in properties of a quantum dot according to the synthesis of a first shell in the quantum dot prepared in the Example 1 of the present disclosure.

It can be seen in FIG. 5A and FIG. 5B that the quantum efficiency of the quantum dot material prepared in the step 1-3 is increased by forming the first shell of Zn—Cu—In—S on the Cu:In(Zn)P core. In addition, it is confirmed in FIG. 5A and FIG. 5B that the first shell is properly grown into a quantum dot having a type-1 core-shell structure considering that the quantum dot material prepared in the step 1-3 exhibits a constant photoluminescence (PL) peak. Here, 'Type-1' structure means that the band gap of the core is included in the band cap of the first shell.

Figure 6A:
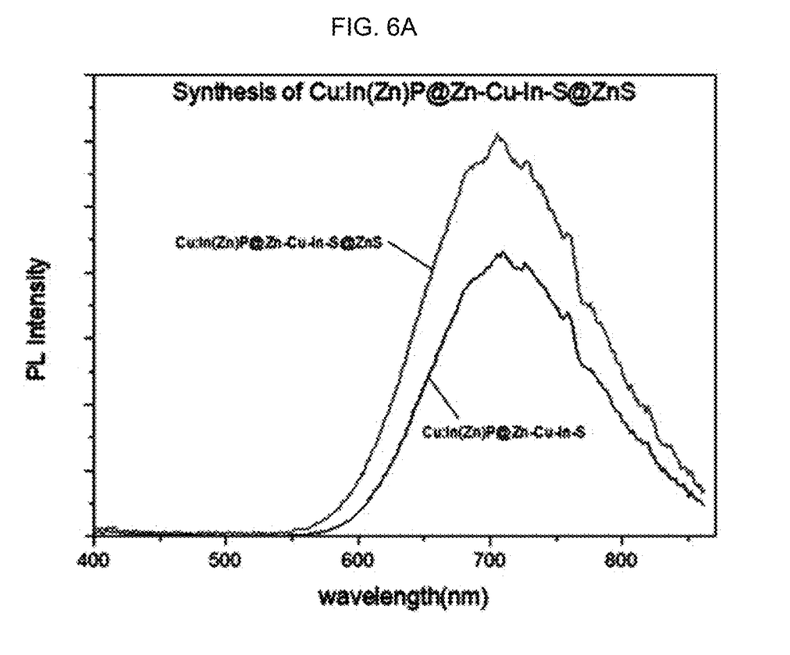
FIG. 6A and FIG. 6B illustrate changes in changes in properties of the quantum dot according to the synthesis of a second shell in the quantum dot prepared in the Example 1 of the present disclosure.
Figure 6B:
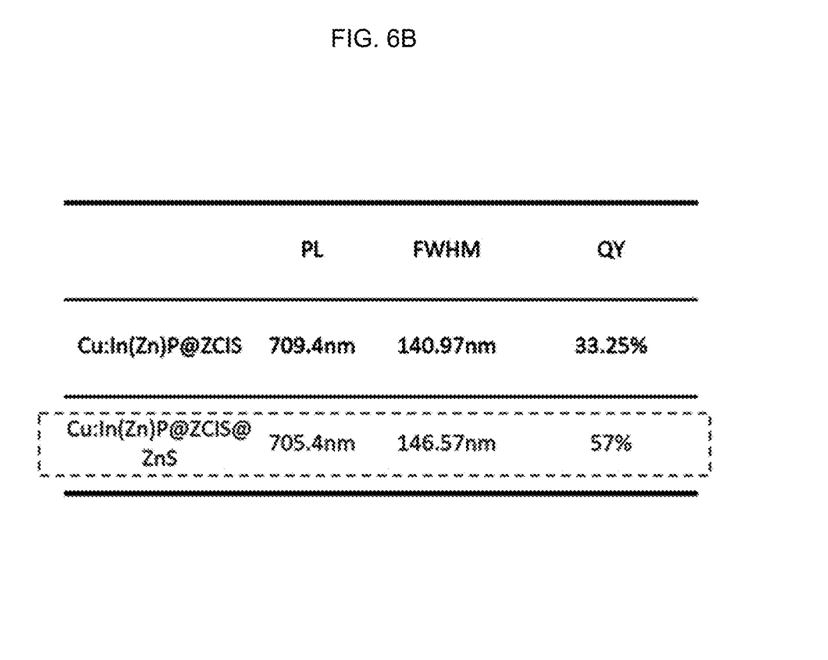

FIG. 6A and FIG. 6B illustrate changes in changes in properties of a quantum dot according to the synthesis of a second shell in the quantum dot prepared in the Example 1 of the present disclosure.

Referring to FIG. 6A and FIG. 6B, the quantum dot prepared in the Example 1 has a structure of Cu:In(Zn)P/Zn—Cu—In—S/ZnS.

It can be seen in FIG. 6A and FIG. 6B that the quantum efficiency of the quantum dot prepared in the Example 1 is significantly increased by overcoating the second shell of ZnS on the Cu:In(Zn)P/Zn—Cu—In—S quantum dot material. In addition, it is confirmed in FIG. 6 that the quantum dot of the Example 1 has the type-2 core-shell structure considering that the quantum dot material prepared in the Example 1 exhibits a constant photoluminescence (PL) peak. Here, 'Type-2' structure means that the band gap of the core is included in the band caps of the first and second shells.

Figure 7:
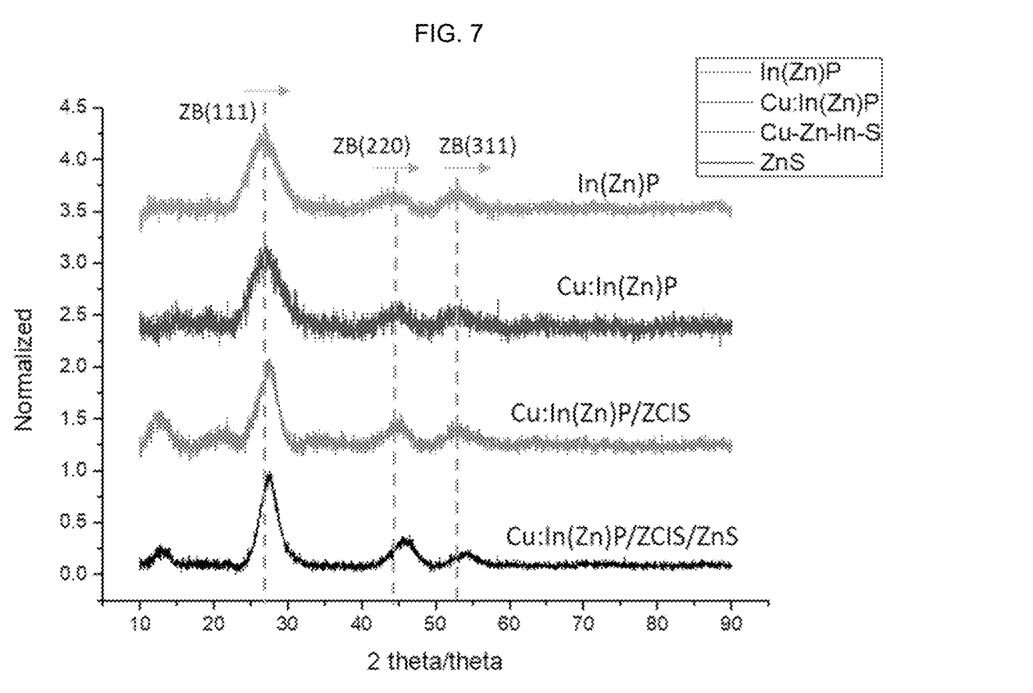
FIG. 7 is a graph showing results of X-Ray Diffraction (XRD) analysis for a quantum dot prepared in each step of the method of manufacturing quantum dot according to Example 1 of the present disclosure.

FIG. 7 is a graph showing results of X-Ray Diffraction (XRD) analysis for the quantum dot prepared in each step of the method of manufacturing quantum dot according to the Example 1 of the present disclosure.

Referring to FIG. 7, the XRD pattern analysis of the materials (i.e. the core material, the core, the quantum dot material, and the quantum dot) synthesized in the steps 1-1 through 1-4 of Example 1 shows that the quantum dot prepared in the Example 1 is formed to have a multi-layer structure.

Three main peaks can be clearly identified from the XRD diffraction pattern of the first shell. Is found that the overall XRD diffraction pattern shifted towards a higher angle side since the lattice constant of In(Zn)P is 5.867, which is the largest, and the lattice constants decrease in the order of Zn—Cu—In—S and ZnS.

Figure 8:
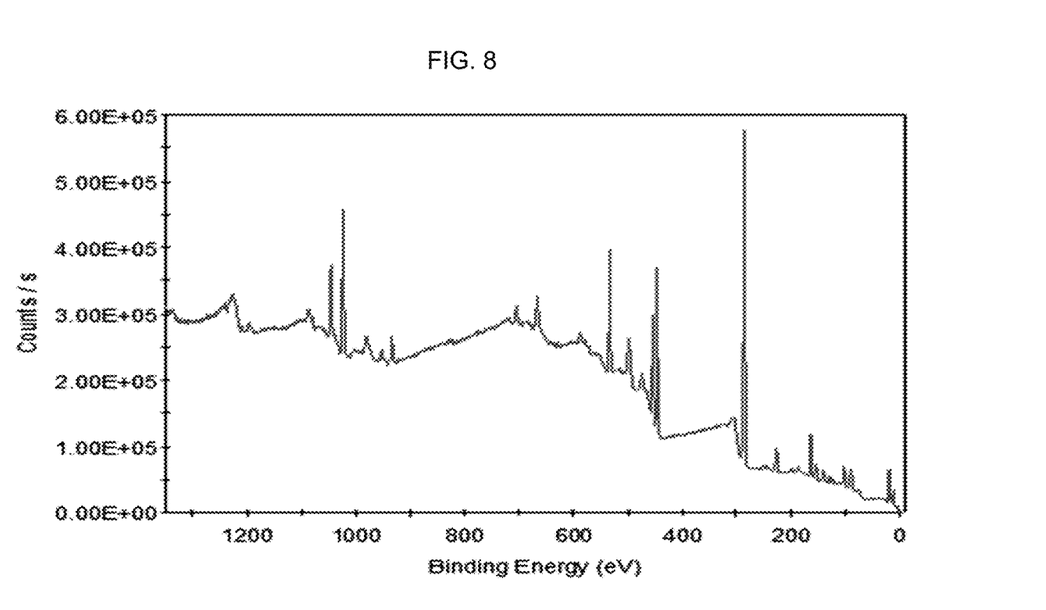
FIG. 8 is a graph showing a XPS analysis result for a first shell of the quantum dot prepared in Example 1 of the present disclosure.
Figure 9:
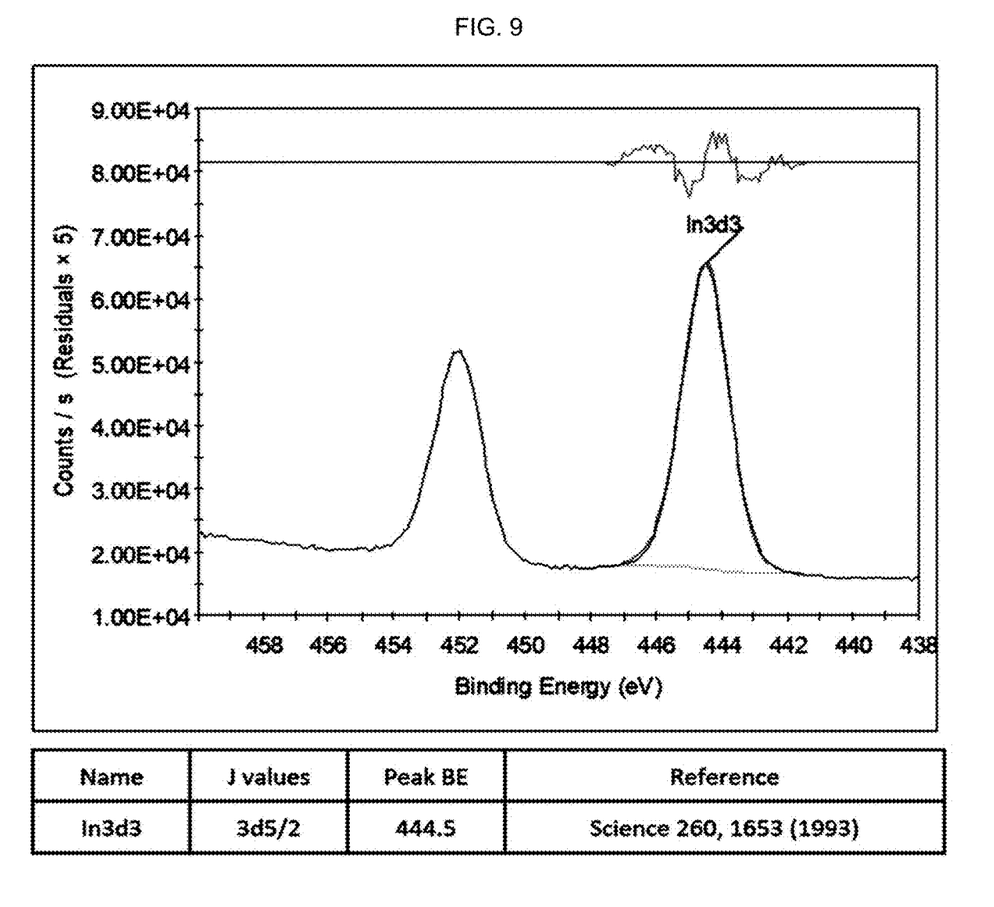
FIG. 9 is a graph showing a XPS analysis result for indium (In) in the first shell of the quantum dot prepared in Example 1 of the present disclosure.
Figure 10:
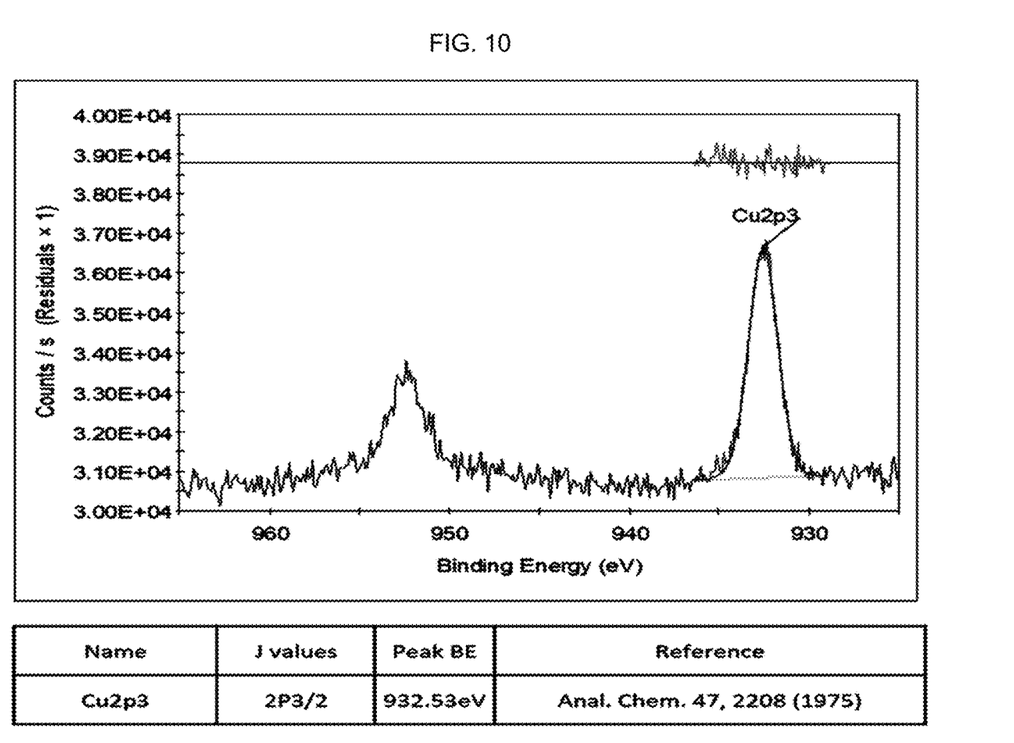
FIG. 10 is a graph showing a XPS analysis result for copper (Cu) in the first shell of the quantum dot prepared in Example 1 of the present disclosure.
Figure 11:
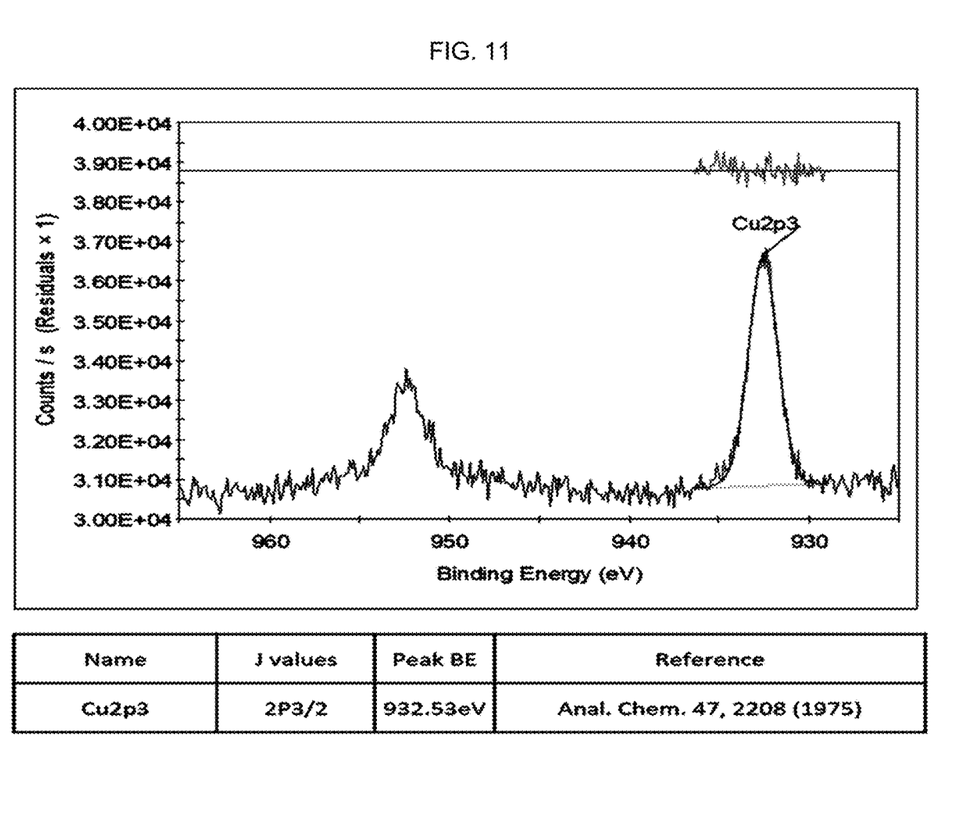
FIG. 11 is a graph showing a XPS analysis result for sulfur (S) in the first shell of the quantum dot prepared in Example 1 of the present disclosure.

FIGS. 8-12 are graphs showing X-ray photoelectron spectroscopy (XPS) elemental analysis results for the first shell of the quantum dot prepared in the Example 1 of the present disclosure. Here, FIG. 8 is a graph showing a XPS analysis result for a first shell of the quantum dot prepared in the Example 1. FIG. 9 is a graph showing a XPS analysis result for indium (In) in the first shell of the quantum dot prepared in the Example 1. FIG. 10 is a graph showing a XPS analysis result for copper (Cu) in the first shell of the quantum dot prepared in the Example 1. FIG. 11 is a graph showing a XPS analysis result for sulfur (S) in the first shell of the quantum dot prepared in the Example 1. FIG. 9 is a graph showing a XPS analysis result for zinc (Zn) in the first shell of the quantum prepared in the Example 1.

Referring to FIG. 8, the elemental analysis for the first shell of Zn—Cu—In—S material by the XPS analysis shows that elements of Zn, Cu, In, and S are present in the first shell.

In the XPS analysis result for the first shell regarding the indium component shown in FIG. 9, increased intensities at 444.5 eV and 452.1 eV correspond to In 3d5/2 and 3d3/2, respectively, which shows that indium 3 corresponds to a chemical structure of the cation. The branching ratio clearly shows 3:2 which is the area ratio of the integral value, and the binding energy gap coincides with 7.54 eV. Such data confirms that indium is present in the first shell.

The XPS analysis result for the first shell regarding the copper component shown in FIG. 10 shows Cu 2P3/2 peak at 932.53 eV and Cu 2P1/2 peak at 452.1 eV that appear in a core level of copper, which shows that copper 1 corresponds to a chemical structure of the cation. Such data confirms that copper is present in the first shell.

The XPS analysis result for the first shell regarding the sulfur component shown in FIG. 11 shows S P3/2 peak at 161.96 eV and S P1/2 peak at 163.14 eV. The branching ratio shows 2:1 which is the area ratio of the integral value, and the binding energy gap coincides with 1.18 eV. Such data confirms that sulfur is present in the first shell.

Figure 12:
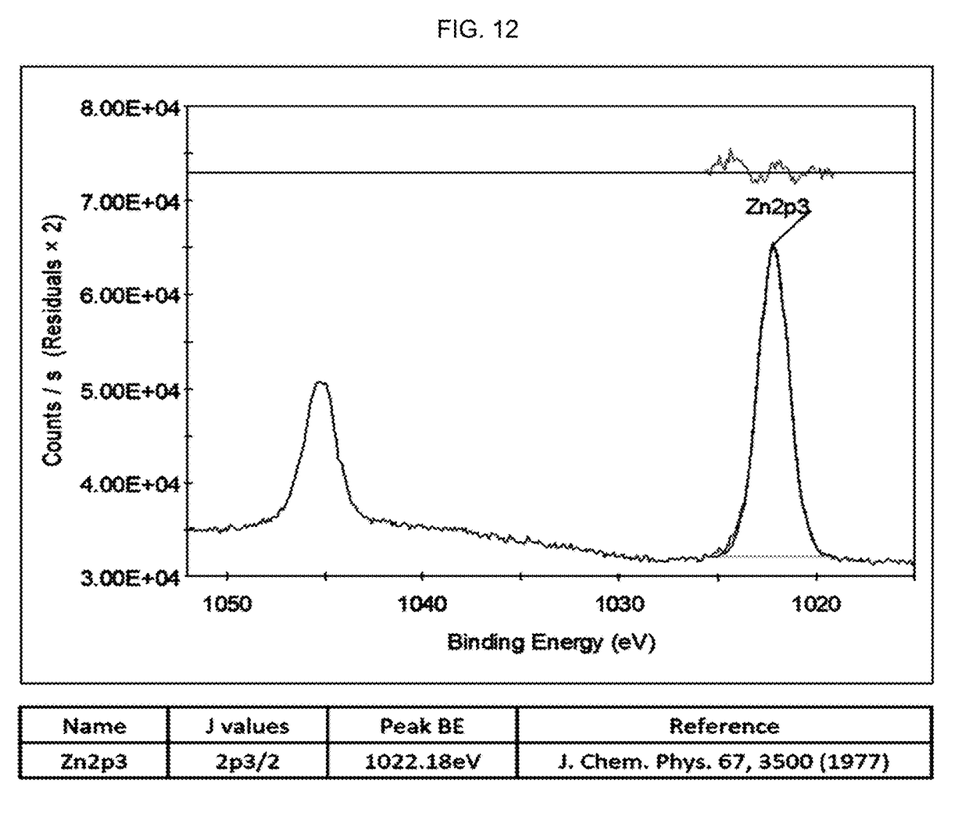
FIG. 12 is a graph showing a XPS analysis result for zinc (Zn) in the first shell of the quantum dot prepared in Example 1 of the present disclosure.

In the XPS analysis result for the first shell regarding the zinc component shown in FIG. 12, increased intensities coincide with shows Zn 2P3/2 peak at 1022.18 eV and Zn 2P1/2 peak at 1045.15 eV. Such data confirms that zinc is present in the first shell.

Figure 13:
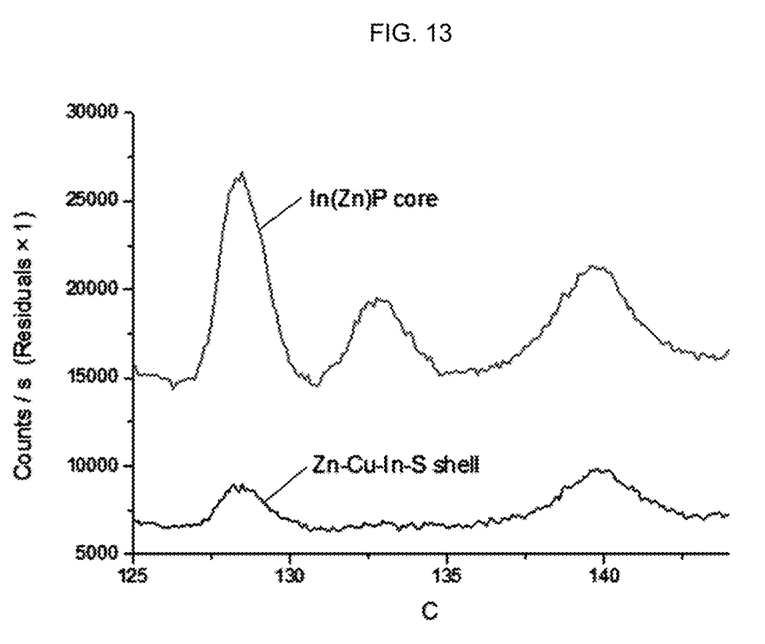
FIG. 13 is a graph showing XPS results for 2P3/2 and 2P1/2 of quantum dots prepared in Example 1 of the present disclosure.

FIG. 13 is a graph showing X-ray spectroscopic analysis (XPS) results for 2P3/2 and 2P1/2 of quantum dots prepared in the Example 1 of the present disclosure.

FIG. 13 shows intensities of the S 2P spectrum of the In(Zn)P core and the core and first shell structure composed of Cu:In(Zn)P/Zn—Cu—In—S. The ratio of P is relatively decreased when the Zn—Cu—In—S first shell is formed on the In(Zn)P core, and thus the ratio of P in the Zn—Cu—In—S shell.

TABLE 1

| Description | Chemical Formula | Indium | Sulfur | Zinc | Phosphorous | Copper |
|---|---|---|---|---|---|---|
| Core | Cu:InP | 3.97 | 0.00 | 3.36 | 1.00 | 0.82 |
| First shell | Cu:InP/ZCIS | 10.49 | 5.63 | 11.82 | 1.00 | 0.92 |
| Second shell | Cu:InP/ZCIS/ZnS | 9.75 | 8.20 | 18.39 | 1.00 | 0.91 |

Table 1 shows quantitative elemental analysis data acquired by an inductively coupled plasma optical emission spectrometry (ICP-OES) analysis. Table 1 shows molar ratio of each element with respect to phosphorous.

For the copper dopant content in the core formed of Cu:InP, a maximum ratio of copper to phosporous (Cu:P), known in the art, 0.196 when ZnSe shell is added. See Renguo Xie et al., *J. Am. Chem. Soc.*, 131 (30): 10645-10651, 2009.

However, when the quantum dot having the structure of Cu:InP/ZCIS/ZnS is formed according to the Example 1, the content ratio of Cu:P is 0.91, which is more than twice higher than the ratio (0.196 that of the quantum dot having the structure of Cu:InP/ZnSe. A high value of 0.82 in the ICP-OES analysis for the core formed of Cu: InP is presumed to be due to an adsorption of copper on the surface of the core during a doping process in which the dopant is absorbed and diffused on the surface of the quantum dot. Considering that the copper content of the first shell-coated core structure (Cu:InP/ZCIS) is increased even though the surface is not influenced when the first shell is formed on the core, the overall copper content is presumed to increase when the first shell is formed.

Also, it is found that molar ratio of Zn, In, Cu, and S is increased remarkably. In addition, it confirmed that the second shell composed of ZnS material is formed properly from the fact that the contents of zinc and sulfur constituting ZnS in the quantum dot having the structure of Cu:InP/ZCIS/ZnS are increased compared with those in the Cu:InP/ZCIS.

Evaluation results of the optical characteristics of the quantum dots manufactured according to the Examples 1 and 2 are shown in Tables 2 and 3.

TABLE 2

|  | Wavelength of photoluminescence peak | Absolute quantum yield | Full width at half maximum (FWHM) |
|---|---|---|---|
| Step 1-1 | 521 nm | 24.70% | 57.5 nm |
| Step 1-2 | 688 nm | 8.9% | 119.25 nm |
| Step 1-3 | 709 nm | 33.25% | 140.97 nm |
| Step 1-4 | 705.4 nm | 57% | 146.57 nm |

Table 2 shows an optical characteristics evaluation result for the core material (step 1-1), the core (step 1-2), the quantum dot material (step 1-3), and the quantum dot (step 1-4) prepared in each step according to the Example 1.

Referring to Table 2, it can be found that the quantum efficiency is improved by forming the first shell and the second shell on the core.

TABLE 3

|  | Wavelength of photoluminescence peak | Absolute quantum yield | Full width at half maximum (FWHM) |
|---|---|---|---|
| Step 2-1 | 567.6 nm | 23.00% | 81.1 nm |
| Step 2-2 | 741 nm | 8% | 157 nm |
| Step 2-3 | 760 nm | 46.7% | 157 nm |
| Step 2-4 | 760 nm | 68% | 167 nm |

Table 3 shows an optical characteristics evaluation result for the core material (step 2-1), the core (step 2-2), the quantum dot material (step 2-3), and the quantum dot (step 2-4) prepared in each step according to the Example 2.

Referring to Table 3, it can be found that the quantum efficiency is improved by forming the first shell and the second shell on the core. In particular, it can be found that the quantum dot according to the Example 2 exhibits a quantum efficiency that is higher by 60% or more.

The description of the disclosure is merely exemplary in nature and, thus, variations that do not depart from the substance of the disclosure are intended to be within the scope of the disclosure. Such variations are not to be regarded as a departure from the spirit and scope of the disclosure.

What is claimed is:

1. A quantum dot having a core-shell structure, comprising:
   a core formed of InZnP material and doped with copper; and
   a shell formed of Cu—Zn—In—S material and surrounding the core.

2. The quantum dot of claim 1, wherein a copper content is 20 wt % or more.

3. The quantum dot of claim 1, wherein a band gap of the core is included in a band gap of the shell.

4. The quantum dot of claim 1, wherein a spectrum shift towards red occurs in an emission wavelength range as a size of the core increases.

5. The quantum dot of claim 1, wherein an emission wavelength range of the core is shifted towards red due to the shell.

6. The quantum dot of claim 1, wherein a quantum efficiency of the quantum dot increases as an increase in a content of indium in the shell, and wherein a change in a peak of the emission wavelength range is within ±5 nm.

7. A quantum dot having a core-shell structure, comprising:
   a core formed of InZnP material and doped with copper;
   a first shell formed of Cu—Zn—In—S material and surrounding the core; and
   a second shell formed ZnS material and surrounding the first shell.

8. The quantum dot of claim 7, wherein a copper content is 20 wt % or more.

9. The quantum dot of claim 7, wherein a band gap of the core is included in band gaps of the first and second shells.

10. The quantum dot of claim 7, wherein a spectrum shift towards red occurs in an emission wavelength range as a size of the core increases.

11. The quantum dot of claim 7, wherein the emission wavelength range of the core is shifted towards red due to the first shell.

* * * * *